US 6,730,631 B1

(12) United States Patent
Eberle et al.

(10) Patent No.: US 6,730,631 B1
(45) Date of Patent: May 4, 2004

(54) METHODS OF PRODUCING MONOLITHIC OXIDATION CATALYSTS AND THEIR USE IN GAS PHASE OXIDATION OF CARBOHYDRATES

(75) Inventors: Hans-Jürgen Eberle, München (DE); Olaf Helmer, München (DE); Karl-Heinz Stocksiefen, Troisdorf/Bergheim (DE); Stefan Trinkhaus, München (DE); Ulrich Wecker, Eurasburg (DE); Norbert Zeitler, München (DE)

(73) Assignee: Consortium für Elektrochemische Industrie GmbH, München (DE)

( * ) Notice: Subject to any disclaimer, the term of this patent is extended or adjusted under 35 U.S.C. 154(b) by 0 days.

(21) Appl. No.: 10/030,614

(22) PCT Filed: Jun. 15, 2000

(86) PCT No.: PCT/EP00/05519

§ 371 (c)(1),
(2), (4) Date: May 3, 2002

(87) PCT Pub. No.: WO01/03832

PCT Pub. Date: Jan. 18, 2001

(30) Foreign Application Priority Data

Jul. 8, 1999 (DE) .......................................... 199 31 902

(51) Int. Cl.⁷ ........................ B01J 21/00; C07D 307/89
(52) U.S. Cl. ...................... 502/350; 502/239; 549/248
(58) Field of Search ................. 502/239, 350; 549/248

(56) References Cited

U.S. PATENT DOCUMENTS

| 4,714,692 A | 12/1987 | Abrevaya et al. |
| 5,792,719 A | 8/1998 | Eberle et al. |
| 6,417,376 B1 * | 7/2002 | Yeh et al. .................. 549/248 |

FOREIGN PATENT DOCUMENTS

| AT | 9201926 | 8/1993 |
| DE | 2 005 969 | 8/1971 |
| DE | 1793 267 | 2/1972 |
| EP | 0 605 142 | 7/1994 |
| EP | 0 744 214 | 7/1999 |
| EP | 0 965 384 | 12/1999 |
| GB | 1274 471 | 5/1972 |

OTHER PUBLICATIONS

Chemical Abstracts, vol. 107, No. 10, p. 335, c1.2, Abstract No. 83172j.
Derwent, Chemical Patents Index, Derwent Publications Ltd., Abstract No. 94–114464114.
Derwent, Chemical Patents Index, Derwent Publications Ltd., Abstract No. 93–321164 141.
Database WPI, Derwent Publications Ltd., AN 1987–012100, XP002151362.
Database WPI, Derwent Publications Ltd., AN 1987–132018, XP00215363.
Chemical Abstracts, vol. 106, No. 24, p. 415, c1.1 Abstract No. 202597t.
English Derwent Abstract AN 1971–56118S Corresponding to DE 2005 969.
English Derwent Abstract AN 1993–321164 Corresponding to AT 9201926.
English Derwent Abstract AN 2000–055432 Corresponding to EP 0 965 384.

* cited by examiner

Primary Examiner—Bernard Dentz
(74) Attorney, Agent, or Firm—Collard & Roe, P.C.

(57) ABSTRACT

A method is for producing monolithic substrate catalysts and for their use in the gas phase oxidation of hydrocarbons. The catalysts are obtained by coating the catalyst substrate with a suspension that includes a catalytically active compound and one or more surfactants of the general formula $R_nY_mX$. R represents the hydrophobic part of the surfactant, with n being 1, 2 or 3. Y represents the hydrophobic part of the surfactant, with m being 0, 1, 2, or 3 and X represents the hydrophilic head group of the surfactant.

19 Claims, No Drawings

METHODS OF PRODUCING MONOLITHIC OXIDATION CATALYSTS AND THEIR USE IN GAS PHASE OXIDATION OF CARBOHYDRATES

CROSS REFERENCE TO RELATED APPLICATIONS

Applicant claims priority under 35 U.S.C. §119 of German Application No. 199 31 902.2 filed Jul. 8, 1999. Applicant also claims priority under 35 U.S.C. 365 of PCT/EP00/05519 filed Jun. 15, 2000. The international application under PCT article 21(2) was not published in English.

BACKGROUND OF THE INVENTION

1. Field of the Invention

The invention relates to a process for producing monolithic oxidation catalysts and to their use in the gas-phase oxidation of hydrocarbons.

2. The Prior Art

Supported catalysts for the gas-phase oxidation of hydrocarbons to give the corresponding oxidation products such as carboxylic acids, carboxylic anhydrides or aldehydes, which catalysts have a catalytically active surface coating consisting essentially of titanium dioxide ($TiO_2$) and divanadium pentoxide ($V_2O_5$), have been known for a long time. A typical example of the use of such catalysts is the preparation of phthalic anhydride, in which mixtures of o-xylene and air or naphthalene and air or o-xylene, naphthalene and air are passed over an appropriate catalyst in a shell-and-tube reactor. The heat generated in this strongly exothermic reaction is customarily removed (cooling, isothermal reaction conditions) by means of a salt melt which surrounds the reaction tubes.

The supported catalysts used here comprise an inert support body, for example having a ring shape or a spherical shape, on which the actual catalytically active composition is present. The active composition consists predominantly of the main components $TiO_2$ in the anatase form and $V_2O_5$. To improve the control of the activity and to improve the selectivity, further activating or deactivating additives, for example oxides of transition elements or alkali metal compounds, are frequently added in small amounts as dopants (promoters) to the catalytically active composition.

The supported catalysts are generally produced by spraying aqueous suspensions or aqueous solutions of $TiO_2$ and $V_2O_5$, frequently with addition of promoters and possibly binders for improving adhesion of the active components to the support, onto the support bodies.

As support bodies, use is made of regularly shaped, mechanically stable bodies such as spheres, rings, half rings, saddles, etc., particularly preferably rings or spheres. The size of the support bodies is determined predominantly by the dimensions of the reactor, especially by the internal diameter of the reaction tubes.

Support materials used are, for example, steatite, Duranit, earthenware, silicon dioxide, silicon carbide, aluminates, metals and metal alloys.

EP-A 744214 (U.S. Pat. No. 5,792,719) discloses a procedure for producing catalysts in which $TiO_2$, $V_2O_5$, SiC and possibly dopants such as $CsCO_3$ and $(NH_4)_2HPO_4$ are stirred in aqueous suspension for a number of hours, and the suspension is subsequently admixed with an organic binder. This suspension is sprayed onto the support material and the supported catalyst is dried.

In industry, it is customary for each of the reaction tubes to be filled with various catalysts which have different catalytically active compositions. These can be arranged, for example, in two superposed zones, an upper zone and a lower zone. This measure makes it possible to match the activity of the catalyst system in the reactor appropriately to the course of the reaction.

During the reaction, the major part of hydrocarbon is reacted in the upper part of the reaction tube. As a result, the highest temperatures inevitably also occur there. In the lower part of the tube, only a sort of after-reaction takes place. There, remaining o-xylene/naphthalene and intermediates, for example o-tolualdehyde and phthalide, are converted into phthalic anhydride. Furthermore, by-products such as quinones are also oxidized further.

As a result of aging processes, all catalysts lose activity as the time for which they have been used increases. This occurs predominantly in the main reaction zone, since this is where the catalyst is subject to the highest temperatures. During the life of the catalyst, the main reaction zone migrates ever further into the catalyst bed. This steadily decreases the length of the remaining catalyst bed and adversely affects the after-reaction. As a consequence, intermediates and by-products can no longer be reacted completely and the product quality of the phthalic anhydride produced therefore deteriorates to an increasing extent. An aging process is particularly critical in the case of high feed loadings. Although the fall-off in the reaction and thus the deterioration in product quality can be countered by increasing the reaction temperature, for example by means of the salt bath temperature, but only to a temperature of about 400° C., this temperature increase is always associated with a loss in yield.

DE-A 1793267 (GB-A 1274471) describes a process for preparing phthalic anhydride, in which the overall oxidative reaction is divided in process engineering terms into two parts. The reaction is controlled so that the reaction conditions in the second part, known as the after-reaction, are significantly more aggressive than in the first part. This can be achieved, for example, by carrying out the after-reaction without cooling, i.e. adiabatically. This after-reaction can be carried out in a separate reactor having different tube dimensions or even in a downstream shaft oven.

DE-A 2005969 describes a process for preparing phthalic anhydride, in which from about 80 to 99% of the total feed is reacted isothermally, i.e. cooled, in the main reaction. Conversion of the remaining unreacted feed occurs in a downstream adiabatic reactor. In addition, in the reaction procedure described, the gas mixture leaving the isothermal reactor is cooled further before it enters the downstream adiabatic reactor. This process variant is likewise intended to enable the phthalic anhydride formed to be obtained largely free of by-products and without a loss in yield. Here too, a shaft oven is claimed as adiabatic reactor.

Owing to the laminar flow occurring in honeycomb catalysts, they have only a very low pressure drop even at very high gas velocities. However, a disadvantage is that, owing to the lack of turbulent flow resulting from the shape, heat and mass transfer in the honeycomb channels, and thus heat removal, are greatly reduced. This situation makes use of honeycomb catalysts as catalyst supports virtually impossible for strongly exothermic processes in conjunction with a selective oxidation. Honeycomb catalysts have therefore become established industrially only in waste gas purification or waste gas incineration where all the organic constituents undergo total oxidation to $CO_2$.

Coating monolithic support material with a catalytically active composition comprising the main constituents $TiO_2$, $V_2O_5$ and possibly dopants by generally known methods, for example a dipping process, is found to be impractical. This is because coating suspensions based on commercially available $TiO_2$ have a very high viscosity even at solids concentrations of 30–35% by weight and thus make coating of the channels of a monolithic support material virtually impossible without blocking the channels.

In order to coat monolithic catalyst supports with the necessary amount of catalytically active composition, for example 50–150 g of active composition per liter of catalyst, the coating process would have to be carried out with such a low-concentration "active composition" suspension that the necessary layer thickness would be achieved only after repeating the coating process a number of times. However, this at the same time once again increases the problem of blocking of the channels in the catalyst support because of the multiple coating steps. Furthermore, this is associated with significantly more work and thus with increased costs and is therefore uneconomical.

SUMMARY OF THE INVENTION

It is therefore an object of the invention to provide a simple and preferably single-stage process for producing monolithic catalysts based on $TiO_2$/metal oxides.

It has now surprisingly been found that the viscosity of highly concentrated $TiO_2$ coating suspensions having a high solids content can be greatly reduced by addition of surfactants The invention provides a process for producing monolithic supported catalysts for gas-phase oxidation by coating the catalyst support by means of a suspension, wherein the latter comprises catalytically active composition comprising one or more types of $TiO_2$ and 1–10% by weight of one or more surfactants of the formula $$R_nY_mX$$

where R is the hydrophobic part(s) of the surfactant and n is 1, 2 or 3; Y is the hydrophilic part of the surfactant and m is 0, 1, 2 or 3, and X is the hydrophilic head group of the surfactant.

The viscosity of highly concentrated $TiO_2$ coating suspensions having a solids content of greater than 30% by weight can be greatly reduced by addition of from 1 to 10% by weight, preferably from 2 to 5% by weight, of surfactants of the formula $R_nY_mX$.

In this formula, R is one or more hydrophobic parts, for example alkyl, aryl and alkylaryl groups, of a surfactant, where n is 1, 2 or 3, preferably 1 or 2. Y is the hydrophilic part of a surfactant, where m is 0, 1, 2 or 3, preferably from 0 to 2. X is the hydrophilic head group of the surfactant.

Preference is given to surfactants having head groups X selected from among phosphates, phosphonates, sulfates, sulfonates and carboxylates, dicarboxylates (malonic acid derivatives, succinic acid derivatives, adipic acid derivatives, maleic acid derivatives, phthalic acid derivatives) and polycarboxylates, for example polyacrylates, polymethacrylates or polymaleic acid derivatives substituted by surfactant radicals (R,Y).

In these head groups X, some of the acid radicals may be present in the H form as free acid groups, in the form of an ammonium salt or as a metal salt. Particular preference is given to free acid groups, ammonium salts and alkaline earth metal salts.

The hydrophilic group Y can be bound to the central atom of the head group X either directly or via an oxygen. Preferred central atoms are carbon, phosphorus and sulfur.

The hydrophobic groups R are preferably bound to the head group via a hydrophilic group Y.

Preferred embodiments of the hydrophobic parts R are alkyl radicals having relatively long-chain carbon building blocks with from 5 to 30 carbon atoms, preferably from 10 to 20 carbon atoms. The alkyl radicals can be saturated or unsaturated or branched carbon chains. The alkyl radicals can be bound directly or via aryl groups to the hydrophilic part Y or the head group X.

The hydrophilic radical Y generally comprises polymeric alkoxy units, preferably propoxy, ethoxy or methoxy units, with the degree of polymerization being able to be from 1 to 50 monomer units, preferably from 5 to 20 monomer units.

The coating suspension used according to the invention can comprise, for example, surfactants of the formula $R_nY_mX$ selected from the group consisting of calcium alkylarylsulfonates., ammonium alkylarylsulfonates, calcium dodecylbenzenesulfonate, polyethoxy(dinonyl phenyl ether phosphate), polyoxoethylene(lauryl ether phosphate), polyethoxy(tridecyl ether phosphate), calcium dodecylbenzenesulfonate, tridecyl phosphate esters, ethoxylated phosphated alcohols, alkyl polyoxyethylene ether phosphate, ammonium nonyl phenyl ether sulfate.

The surfactants can be used without addition of further surfactants or together with other surfactants, for example alkylphenol ethoxylate.

The addition according to the invention of the surfactants to the coating suspension allows low-viscosity coating suspensions having high solids contents of $TiO_2$ and/or $V_2O_5$ to be prepared and to be used for coating monolithic support material, for example honeycombs and supports having open or closed cross-channel structures. The coating suspensions may further comprise other additives, for example SiC. The solids contents of catalytically active composition in such suspensions can be set to values of up to 50% by weight and above. Such highly concentrated suspensions allow monolithic and, in particular, honeycomb catalyst supports coated with from 50 to 150 g of active composition per liter of honeycomb catalyst to be obtained without problems in one coating step.

Suspensions having a solids content of $TiO_2$ of greater than 35% by weight have, owing to the high viscosity, greatly reduced flow and can therefore no longer flow through narrow channels. Changing to larger particle sizes does not lead to success either. The addition of one or more of the surfactants claimed significantly improves flow.

The catalysts of the invention can be produced using uniform $TiO_2$ grades or mixtures of various $TiO_2$ grades, which may in turn be doped or coated with metal oxides. The active composition preferably comprises $V_2O_5$ as additional component.

The coating of honeycombs with coating suspensions without addition of surfactants can be carried out without problems only using suspensions having a relatively low solids content of about 30% by weight. However, the amounts of active composition which can be applied in this way are only about 20 g/l of catalyst. If the solids content is slightly increased, the viscosity of the suspension increases so much that the suspension can no longer flow out of the honeycomb channels and blocking of the channels therefore results.

The use of the surfactants claimed enables the honeycombs to be coated without problems even using suspensions containing more than 50% by weight of active composition.

Applied amounts of over 100 g of solid/l of honeycomb catalyst can be achieved without problems in one coating step when using the surfactants claimed.

Examples of support materials suitable for coating by the process of the invention are materials such as cordierite, silicates, silicon dioxide, silicon carbide, aluminum oxide, aluminates or mixtures of these materials and metals or metal alloys. The support bodies can also have closed or open cross-channel structures. The suspensions used according to the invention enable honeycombs having a high to very high cell density to be coated without the danger of blocking the channels.

Preference is given to honeycombs having a cell density, i.e. a number of channels, of from 100 to 400 csi (cells per square inch), particularly preferably from 100 to 200 csi.

Monolithic catalysts are very well suited to the selective oxidation of o-xylene/air mixtures having low o-xylene contents to give PA. The monolithic catalysts do not in any event have a tendency to produce a runaway reaction. Surprisingly, the monolithic catalysts are superior to the conventional ring catalyst (for the same active composition).

Catalysts produced according to the invention and having a content of active composition of from 40 to 200 g per liter of catalyst are particularly advantageous. At a comparable temperature, these achieve higher conversions, better PA selectivities and smaller amounts of by-products.

The honeycomb catalysts produced according to the invention are very useful as catalysts for an after-reaction of a PA process gas comprising one or more of the starting materials o-xylene and naphthalene and/or intermediates such as tolualdehyde, phthalide, naphthoquinone, etc. This reaction is advantageously carried out at lower gas inlet temperatures, based on the temperature of the main reactor. In this after-reaction, a major part of the underoxidation products can be removed from the reaction gas and reacted further to form PA. Surprisingly, this also occurs at relatively high space velocities of 20,000–30,000 h$^{-1}$. Even in the presence of relatively high contents of underoxidation products together with a high concentration of PA, no runaway reaction occurs when using the catalysts of the invention.

The monolithic catalysts produced according to the invention are particularly suitable for preparing phthalic anhydride in an adiabatic reactor (after-reactor) in combination with an isothermally operated reactor (main reactor, for example filled with a bed of particulate catalyst).

The adiabatic reactor can also be operated advantageously with upstream gas cooling. In a particularly preferred embodiment, the upstream gas cooling and the adiabatic reaction are carried out in a joint apparatus.

In industry, it is customary to cool the reaction gas in a gas cooler before isolation of the product. The upstream gas cooling, the adiabatic reaction in the monolithic catalyst bed and further cooling can be carried out within the reactor or, outside the reactor, or in a joint apparatus.

DETAILED DESCRIPTION OF THE PREFERRED EMBODIMENTS

The invention is illustrated in more detail by the following examples.

The following examples demonstrate the influence of surfactants from the group consisting of phosphoric esters on the viscosity of support oxide suspensions. The flow behavior of the suspensions prepared was determined by a method based on DIN 53211 using a flow cup. Two types of TiO$_2$ which differed from one another only in the particle size were tested. The mean particle diameter was 0.1 and 0.4 μm, respectively. This measurement method was selected since it could appropriately simulate flow of a suspension out of the honeycomb channels. As outflow nozzle, use was made of a nozzle having a diameter of 2 mm corresponding to a flow orifice area of 3.14 mm$^2$. For comparison, a 200 csi honeycomb has a channel cross section of 2.3 mm$^2$ and a 100 csi honeycomb has a channel cross section of 4.66 mm$^2$. If the viscosity of the suspension was too high, i.e. the suspension could not flow through the nozzle under these conditions, the experiment was repeated using a nozzle opening of 4 mm diameter. If no outflow of the suspension could be measured even under the altered conditions, the experiment was evaluated as "not measurable".

COMPARATIVE EXAMPLE 1

(30% Strength by Weight Suspension Without Surfactant):

A suspension was prepared from a mixture of 30 g of TiO$_2$ having a mean particle diameter of 0.1 μm and 70 g of water and was stirred for 2 hours. The flow was subsequently measured in the flow cup. At a nozzle diameter of 2 mm, the outflow rate was 1.4 ml/sec.

COMPARATIVE EXAMPLE 2

(33% Strength by Weight Suspension Without Surfactant):

A suspension was prepared from a mixture of 33 g of TiO$_2$ having a mean particle diameter of 0.1 μm and 67 g of water and was stirred for 2 hours. The flow was subsequently measured in the flow cup. At a nozzle diameter of 2 mm, no outflow was observed. At a nozzle diameter of 4 mm, the outflow rate was 6.2 ml/sec.

COMPARATIVE EXAMPLE 3

(22% Strength by Weight Suspension Without Surfactant):

A suspension was prepared from a mixture of 22 g of TiO$_2$ having a mean particle diameter of 0.4 μm and 78 g of water and was stirred for 2 hours. The flow was subsequently measured in the flow cup. At a nozzle diameter of 2 mm, the outflow rate was 1.7 ml/sec.

COMPARATIVE EXAMPLE 4

(25% Strength by Weight Suspension Without Surfactant):

A suspension was prepared from a mixture of 25 g of TiO$_2$ having a mean particle diameter of 0.4 μm and 75 g of water and was stirred for 2 hours. The flow was subsequently measured in the flow cup. At a nozzle diameter of 2 mm, no outflow was observed. At a nozzle diameter of 4 mm, the outflow rate was 8.3 ml/sec.

EXAMPLE 5

(45% Strength by Weight Suspension):

A suspension was prepared from a mixture of 45 g of TiO$_2$ having a mean particle diameter of 0.1 μm, 55 g of water and 3.5 g of alkyl(C$_8$–C$_{10}$)polyoxyethylene ether phosphate and was stirred for 2 hours. The flow was subsequently measured in the flow cup. At a nozzle diameter of 2 mm, the outflow rate was 0.9 ml/sec.

EXAMPLE 6

(45% Strength by Weight Suspension):

A suspension was prepared from a mixture of 45 g of TiO$_2$ having a mean particle diameter of 0.4 μm, 55 g of water and 3.0 g of alkyl(C$_8$–C$_{10}$)polyoxyethylene ether phosphate and was stirred for 2 hours. The flow was subsequently measured in the flow cup. At a nozzle diameter of 2 mm, the outflow rate was 2.0 ml/sec.

EXAMPLE 7

(45% Strength by Weight Suspension):

A suspension was prepared from a mixture of 45 g of TiO$_2$ having a mean particle diameter of 0.4 μm, 55 g of water and 5.0 g of polyethoxydinonylphenyl ether phosphate and was stirred for 2 hours. The flow was subsequently measured in the flow cup. At a nozzle diameter of 2 mm, the outflow rate was 1.2 ml/sec.

EXAMPLE 8
(45% Strength by Weight Suspension):

A suspension was prepared from a mixture of 45 g of $TiO_2$ having a mean particle diameter of 0.4 μm, 55 g of water and 2.0 g of a mixture of alkylphenol ethoxylate/calcium alkylarylsulfonate and was stirred for 2 hours. The flow was subsequently measured in the flow cup. At a nozzle diameter of 2 mm, the outflow rate was 1.3 ml/sec.

EXAMPLE 9
(45% Strength by Weight Suspension):

A suspension was prepared from a mixture of 45 g of $TiO_2$ having a mean particle diameter of 0.1 μm, 55 g of water and 5.0 g of calcium dodecylbenzenesulfonate and was stirred for 2 hours. The flow was subsequently measured in the flow cup. At a nozzle diameter of 2 mm, the outflow rate was 0.5 ml/sec.

EXAMPLE 10
(45% Strength by Weight Suspension):

A suspension was prepared from a mixture of 45 g of $TiO_2$ having a mean particle diameter of 0.4 μm, 55 g of water and 2.5 g of ammonium nonyl phenyl ether sulfate and was stirred for 2 hours. The flow was subsequently measured in the flow cup. At a nozzle diameter of 2 mm, the outflow rate was 1.8 ml/sec.

COMPARATIVE EXAMPLE 11

A suspension was prepared from a mixture of 38 g of $TiO_2$ having a mean particle diameter of 0.4 μm, 9.5 g of $V_2O_5$ and 46.8 g of water and was stirred for 2 hours. The flow was subsequently measured in the flow cup. The outflow rate could be measured neither using a 2 mm nozzle opening nor a 4 mm nozzle opening, since the viscosity of the suspension was too high in both cases.

EXAMPLE 12

A suspension was prepared from a mixture of 38 g of $TiO_2$ having a mean particle diameter of 0.4 μm, 9.5 g of $V_2O_5$, 46.8 g of water and 3 g of alkyl($C_8$–$C_{10}$)polyoxyethylene ether phosphate and was stirred for 2 hours. The flow was subsequently measured in the flow cup. At a nozzle diameter of 2 mm, the outflow rate was 1.3 ml/sec.

Examples 13 to 17 below demonstrate the production of catalysts by way of coating experiments on appropriate monolithic support bodies.

COMPARATIVE EXAMPLE 13
(Without Addition of Surfactant):

354 g of $TiO_2$ (BET about 30 $m^2/g$) having a mean particle diameter of 0.1 μm, 118 g of $TiO_2$ (BET<10 $m^2/g$) having a mean particle diameter of 0.4 μm, 120 g of $V_2O_5$ and 8.24 g of $(NH_4)_2HPO_4$ were suspended in 1400 ml of deionized water and stirred for 18 hours to achieve homogeneous dispersion. The solids content of the suspension obtained was 29.6% by weight. 60 g of organic binder, namely a copolymer of vinyl acetate and vinyl laurate, in the form of a 50% strength by weight aqueous dispersion were then added. A monolithic ceramic support honeycomb made of cordierite and having a cell density of 200 cpsi and dimensions of 7.5 cm×7.5 cm×15 cm was then dipped into this coating suspension and taken from the dipping bath after about 1 minute. The residues of suspension present in the channels were blown out using an air blower (at not more than 130° C.). Complete drying of the coated honeycomb was carried out in a drying oven at 130° C. for 12 hours. The amount of active composition applied was 20 g/l of catalyst. The honeycomb was just able to be coated.

COMPARATIVE EXAMPLE 14
(Without Addition of Surfactant):

To produce a catalyst coated with a larger amount of active composition, 354 g of $TiO_2$ (BET about 30 $cm^2/g$) having a mean particle diameter of 0.1 μm, 118 g of $TiO_2$ (BET<10 $m^2/g$) having a mean particle diameter of 0.4 μm, 120 g of $V_2O_5$ and 8.24 g of $(NH_4)_2HPO_4$ were suspended in 1220 ml of deionized water and stirred for 18 hours to achieve homogeneous: dispersion. The solids content of the suspension obtained was 32.7% by weight. 60 g of organic binder, namely a copolymer of vinyl acetate and vinyl laurate, in the form of a 50% strength by weight aqueous dispersion were then added. Using this coating suspension, a monolithic ceramic support honeycomb made of cordierite and having a cell density of 200 cpsi and dimensions of 7.5 cm×7.5 cm×15 cm was coated using a method analogous to Example 15. In this example, the suspension was so highly viscous that the channels could not be freed completely of excess suspension even with the aid of the blower. About 10% of the channels remained blocked. The coated honeycomb could not be used as a catalyst.

COMPARATIVE EXAMPLE 15
(Coating of Rings)

To produce a ring-shaped comparative catalyst, 73.7 g of $TiO_2$ (BET about 30 $m^2/g$) having a mean particle diameter of 0.1 μm, 24.6 g of $TiO_2$ (BET<10 $m^2/g$) having a mean particle diameter of 0.4 μm, 25 g of $V_2O_5$ and 1.7 g of $(NH_4)_2HPO_4$ were suspended in 400 ml of deionized water and stirred for 18 hours to achieve homogeneous dispersion. 6.2 g of organic binder, namely a copolymer of vinyl acetate and vinyl laurate, in the form of a 50% strength by weight aqueous dispersion were then added. All of this coating suspension was applied to 1225 g of steatite rings (7×7×4 mm) as support material with evaporation of the water. The layer thickness of active composition was about 60 μm.

EXAMPLE 16
(Catalyst 1 According to the Invention):

602 g of $TiO_2$ (BET about 30 $m^2/g$) having a mean particle diameter of 0.1 μm, 200 g of $TiO_2$ (BET<10 $m^2/g$) having a mean particle diameter of 0.4 μm, 204 g of $V_2O_5$ and 70 g of alkyl($C_8$–$C_{10}$)polyoxyethylene ether phosphate were suspended in 980 ml of deionized water and stirred for 18 hours to achieve homogeneous dispersion. The solids content of the suspension obtained was 51% by weight 60 g of organic binder, namely a copolymer of vinyl acetate and vinyl laurate, in the form of a 50% strength by weight aqueous dispersion were then added. Using this coating suspension, a monolithic ceramic support honeycomb made of cordierite and having a cell density of 200 cpsi and dimensions of 7.5 cm×7.5 cm×15 cm was coated using a method analogous to Example 15. Due to the viscosity-lowering action of the surfactant, the suspension not adhering to the wall flowed completely out of the channels without problems. Owing to the high solids content of the suspension used, 115 g of active composition per liter of catalyst could be applied in a single coating step. No channels of the honeycomb were blocked with active composition. The layer thickness of active composition was about 60 μm.

EXAMPLE 17

(Catalyst 2 According to the Invention):

602 g of $TiO_2$ (BET about 30 $m^2/g$) having a mean particle diameter of 0.1 µm, 220 g of $V_2O_5$ and 120 g of calcium dodecylbenzenesulfonate were suspended in 885 ml of deionized water and stirred for 18 hours to achieve homogeneous dispersion. The solids content of the suspension obtained was 50% by weight. 60 g of organic binder, namely a copolymer of vinyl acetate and vinyl laurate, in the form of a 50% strength by weight aqueous dispersion were then added. Using this coating suspension, a monolithic ceramic support honeycomb made of cordierite and having a cell density of 200 cpsi and dimensions of 7.5 cm×7.5 cm×15 cm was coated using a method analogous to Example 15. Due to the viscosity-lowering action of the surfactant, the suspension not adhering to the wall flowed completely out of the channels without problems. Owing to the high solids content of the suspension used, 108 g of active composition per liter of catalyst could be applied in a single coating step. No channels of the honeycomb were blocked with active composition.

EXAMPLE 18

(Catalyst 3 According to the Invention):

To produce a catalyst based on a $TiO_2$ having a larger mean particle diameter, 785 g of $TiO_2$ (BET about 30 $m^2/g$) having a mean particle diameter of 0.4 µm, 196 g of $V_2O_5$ and 46 g of alkyl($C_8$–$C_{10}$)polyoxyethylene ether phosphate were suspended in 910 ml of deionized water and stirred for 18 hours to achieve homogeneous dispersion. The solids content of the suspension obtained was 52% by weight. 60 g of organic binder, namely a copolymer of vinyl acetate and vinyl laurate, in the form of a 50% strength by weight aqueous dispersion were then added. Using this coating suspension, a monolithic ceramic support honeycomb made of cordierite and having a cell density of 200 cpsi and dimensions of 7.5 cm×7.5 cm×15 cm was coated using a method analogous to Example 15. Due to the viscosity-lowering action of the surfactant, the suspension not adhering to the wall flowed completely out of the channels without problems. Owing to the high solids content of the suspension used, 97 g of active composition per liter of catalyst could be applied in a single coating step. No channels of the honeycomb were blocked with active composition.

EXAMPLE 19

(Oxidation of O-xylene/Air Mixtures Having a Low O-xylene Concentration):

To examine the catalytic properties, the catalysts were tested for suitability in (by way of example) the oxidation of o-xylene and compared to a conventional catalyst produced according to the prior art (ring-shaped catalysts). The test apparatus used comprised an adiabatic, i.e. uncooled, insulated reactor. The reactor was constructed so that it could be charged both with catalyst rings and with a honeycomb catalyst according to the invention. An air preheater by means of which the o-xylene/air mixture could be heated to 300–360° C. was installed upstream of the reactor. The cross-sectional inflow area of the catalyst was 19.6 $cm^2$ and the catalyst fill height was 10.2 cm. The experiments were carried out at a space velocity of 20,000 $h^{-1}$. The concentration of o-xylene in the gas mixture at the reactor inlet was in the range from 500 to 600 mg/standard $m^3$. The o-xylene concentration was measured by means of gas chromatography and also an on-line FID detector. The reaction gas leaving the reactor was collected in acetone and the constituents were determined quantitatively by means of gas chromatography. The content of carbon monoxide and carbon dioxide in the outlet gas from the reactor was determined directly by means of infrared measurement.

The catalysts from Comparative Example 13 and from Example 16, and also a ring-shaped catalyst (Example 15) as further comparison, were tested using the above-described apparatus. The active compositions of all three catalysts had the same chemical composition.

The test results are summarized in Table 1 below.

TABLE 1

Catalyst tests using low-concentration o-xylene/air mixtures

| | Comparative catalyst on rings (Example 15) | Honeycomb catalyst with 20 g of active composition/1 of catalyst (Example 13) | Honeycomb catalyst according to the invention with 112 g of active composition/1 of catalyst (Example 16) |
|---|---|---|---|
| Temperature at gas inlet | 340° C. | 340° C. | 340° C. |
| o-xylene conversion/mol % | 56 | 82 | 95 |
| PA selectivity/mol % | 41 | 62 | 67 |
| O-tolualdehyde/mg/Standard $m^3$ | 22 | 42 | 12 |
| Phthalide mg/Standard $m^3$ | 20 | 36 | 14 |

EXAMPLE 20

(Suitability of the Monolithic Catalysts Produced According to the Invention for (by Way of Example) the After-reaction of PA Process Gas From O-xylene Oxidation in a Post-reactor):

The test apparatus used (post-reactor) comprised an adiabatically operated (well insulated) reaction tube in which the monolithic catalyst of the invention from Example 18 was installed. The post-reactor was installed downstream of a customary PA pilot reactor (main reactor). The gas line between main reactor and post-reactor could be thermostatted so that variable gas inlet temperatures into the post-reactor were possible. Gas sampling points were installed before the inlet and at the outlet of the post-reactor. Furthermore, the reaction gas could be cooled in a condenser (desublimator) either after leaving the main reactor or after leaving the post-reactor and the PA formed could be deposited or isolated. The main PA reactor was 3.3 m long and had a tube diameter of 25 mm. The temperature of the reactor was regulated using a circulated salt bath (eutectic melt of potassium nitrate and sodium nitrite). The amount of air fed in was always 4 standard $m^3$/h. The main PA reactor was charged with a commercial PA catalyst and the catalyst fill height was 2.8 m. The salt bath temperatures were selected so that the gas mixture leaving the reactor still had comparatively high contents of unreacted o-xylene and underoxidation products such as phthalide and tolualdehyde. The o-xylene loading upstream of the reactor was constant at 70 g/Standard $m^3$ of gas during the experiments. The air/o-xylene mixture was preheated to 180° C. before entering the main reactor.

The reaction gas leaving the main reactor was brought to the desired temperature by means of thermostatting and passed through the post-reactor containing the monolithic catalyst. The amount of monolithic catalyst was selected so that a space velocity of 20,000 $h^{-1}$ resulted.

The reaction gas leaving the post-reactor was subsequently passed through a desublimator in order to deposit the reaction products PA, phthalide, etc.

In order to be able to assess the efficiency of the post-reactor in respect of degradation or further oxidation of the by-products, part of the PA reaction gas both before and after the post-reactor was analyzed by scrubbing the gas in acetone and subsequently determining the o-xylene, phthalide and tolualdehyde contents by gas chromatography. The CO and $CO_2$ contents in the reaction gas before and after the post-reactor were measured by IR spectroscopy. The PA yield was, as already mentioned, determined by means of deposition in a desublimator or calculated via a mass balance.

The results of the experiments are shown in Table 2 below.

TABLE 2

Results of the oxidation experiments on PA reaction gas

| | Contents* before/without post-reactor | Contents* in % by weight after post-reactor with catalyst from Ex. 18 at various gas inlet temperatures | | | |
|---|---|---|---|---|---|
| | | 360° C. | 340° C. | 320° C. | 300° C. |
| Phthalide | 0.48% by weight | 0.005 | 0.014 | 0.041 | 0.101 |
| o-Xylene | 0.25% by weight | 0 | 0.004 | 0.022 | 0.081 |
| p-Benzo-quinone | 0.04% by weight | 0.012 | 0.015 | 0.019 | 0.022 |
| o-Tolual-dehyde | 0.21% by weight | 0 | 0.004 | 0.011 | 0.026 |
| PA yield | 111.0% by weight | 111.3 | 111.5 | 111.8 | 112.2 |

*Based on the total organic constituents in the reaction gas.

The results in Table 2 show that a major part of the underoxidation products can be removed from the reaction gas and oxidized further to PA by using the monolithic catalysts of the invention in a downstream adiabatic reactor (post-reactor) in the PA process. Surprisingly, this also takes place at relatively high space velocities. To achieve the best yield, the after-reaction is advantageously carried out at low gas inlet temperatures. The optimum reaction conditions are a compromise between yield and amount of by-products.

EXAMPLE 21

(Suitability of the Monolithic Catalysts Produced According to the Invention for (by Way of Example) the After-reaction of PA Process Gas From Naphthalene Oxidation in a Post-reactor)

The experiment was carried out using a method analogous to Example 20, except that the main reactor was charged with a commercial PA catalyst suitable for naphthalene oxidation and was supplied with a naphthalene/air mixture. The monolithic catalyst of the invention from Example 18 was installed in the post-reactor. In this example too, the salt bath temperature in the main reactor was selected so that the gas mixture leaving the reactor still had comparatively high contents of unreacted naphthalene and the by-product naphthoquinone. The naphthalene loading of the feed to the main reactor was a constant 70 g/Standard $m^3$ at 4 standard $m^3$ of gas/h during the experiment.

The results of the experiment are shown in Table 3 below.

TABLE 3

Results of the oxidation experiments on PA reaction gas from naphthalene oxidation

| | Contents* before/without post-reactor | Contents* after post-reactor with catalyst from Ex. 18 at a gas inlet temperature of 350° C. |
|---|---|---|
| Naphthalene | 0.12% by weight | 0.02% by weight |
| Naphthoquinone | 0.54% by weight | 0.06% by weight |
| PA yield | 99.7% by weight | 100.3% by weight |

*Based on the total organic constituents in the reaction gas.

The results in Table 3 show that, in the PA process using naphthalene as feed, a major part of the residual naphthalene and the by-product naphthoquinone can be removed from the reaction gas and oxidized further to PA by using the monolithic catalysts of the invention in a downstream adiabatic reactor (post-reactor).

What is claimed is:

1. A process for producing monolithic supported catalysts for gas-phase oxidation comprising
   coating a catalyst support with a suspension,
   wherein the suspension comprises catalytically active composition comprising at least one type of $TiO_2$ and 1–10% by weight of at least one surfactant of the formula $R_nY_mX$ where R is a hydrophobic group of the surfactant and n is 1, 2 or 3; Y is a hydrophilic group of the surfactant and m is 0, 1, 2 or 3, and X is a hydrophilic head group of the surfactant; and the percent by weight is based upon the total weight of the compositions;
      wherein the head group X present in the surfactant is a functional group selected from the group consisting of carboxylate, polycarboxylate, phosphate, phosphonate, sulfate and sulfonate; and
      wherein hydrophobic groups R of the surfactant used are selected from the group consisting of saturated alkyl radicals with carbon building blocks having from 5 to 30 carbon atoms, unsaturated alkyl radicals with carbon building blocks having from 5 to 30 carbon atoms; and
   branched alkyl radicals with carbon building blocks having from 5 to 30 carbon atoms and are bound either directly or via aryl groups to a group selected from the group consisting of the hydrophilic group Y and the head group X.

2. The process as claimed in claim 1,
   wherein the surfactant comprises from 2 to 5% by weight based upon the total weight.

3. The process as claimed in claim 1,
   wherein at least one of the functional groups of the head group X is selected from the group consisting of free acid group, ammonium salt, and alkaline earth metal salt.

4. The process as claimed in claim 1,
   wherein the hydrophilic group Y is bound to a central atom of the head group X either directly or via an oxygen.

5. The process as claimed in claim 1,
   wherein the hydrophobic group R of the surfactant used is bound to the head group X via a hydrophilic group Y.

6. The process as claimed in claim 1,
wherein the hydrophilic group Y of the surfactants used comprises polymeric alkoxy units whose degree of polymerization is from 1 to 50 monomer units.

7. The process as claimed in claim 1,
wherein said at least one surfactant is selected from the group consisting of calcium alkylarylsulfonate, alkylphenol ethoxylate, ammonium alkylarylsulfonate, calcium dodecylbenzenesulfonate, polyethoxy (dinonyl phenyl ether phosphate), polyoxoethylene (lauryl ether phosphate), polyethoxy (tridecyl ether phosphate), calcium dodecylbenzenesulfonate, tridecyl phosphate ester, ethoxylated phosphated alcohol, alkyl polyoxyethylene ether phosphate, and ammonium nonyl phenyl ether sulfate.

8. The process as claimed in claim 1,
wherein the catalytically active composition further comprises $V_2O_5$ as an additional component.

9. The process as claimed in claim 1,
wherein the catalytically active composition comprises promoters.

10. The process as claimed in claim 1,
wherein the catalyst support used is at least one material selected from the group consisting of cordierite, silicate, silicon dioxide, silicon carbide, aluminum oxide, aluminate, metal and metal alloy.

11. The process as claimed in claim 1,
wherein a catalyst support body used is selected from the group consisting of a honeycomb, a support having open cross-channel structure, a support having closed cross channel structure, and mixtures thereof.

12. The process as claimed in claim 11, wherein
wherein the catalyst support body used is a honeycomb having a cell density of a number of channels, of from 100 to 400 csi (cells per square inch).

13. A method for preparing phthalic anhydride comprising
a gas-phase oxidation reaction of o-xylene by contacting said o-xylene with a monolithic supported catalyst obtainable by the process as claimed in claim 1 in an adiabatic reactor in combination with an isothermally operated reactor.

14. A method for preparing phthalic anhydride comprising
a gas-phase oxidation reaction of naphthalene by contacting said naphthalene with a monolithic supported catalyst obtainable by the process as claimed in claim 1 in an adiabatic reactor in combination with an isothermally operated reactor.

15. A method for preparing phthalic anhydride comprising
a gas-phase oxidation reaction of a mixture of o-xylene and naphthalene by contacting said mixture of o-xylene and naphthalene with a monolithic supported catalyst obtainable by the process as claimed in claim 1 in an adiabatic reactor in combination with an isothermally operated reactor.

16. The method as claimed in claim 13,
wherein the adiabatic reactor has upstream gas cooling in combination with an isothermally operated reactor.

17. The method as claimed in claim 13,
wherein the adiabatic reactor has upstream gas cooling, where gas cooling and the reaction are carried out in a joint apparatus, in combination with an isothermally operated reactor.

18. The method as claimed in claim 13,
wherein the adiabatic reactor has upstream gas cooling and downstream gas cooling, where gas cooling and the reaction are carried out in a joint apparatus, in combination with an isothermally operated reactor.

19. A monolithic catalyst comprising
a catalyst support coated with a suspension; and said suspension comprises a catalytically active composition comprising
at least one type of $TiO_2$ and 1–10% by weight of at least one surfactant of the formula $$R_nY_mX$$

where R is a hydrophobic group of the surfactant and n is 1, 2 or 3; Y is a hydrophilic group of the surfactant and m is 0, 1, 2 or 3, and X is a hydrophilic head group of the surfactant; and
the percent by weight is based upon the total composition weight; and
wherein the head group X present in the surfactant is a functional group selected from the group consisting of carboxylate, polycarboxylate, phosphate, phosphonate, sulfate and sulfonate;
wherein hydrophobic groups R of the surfactant used are selected from the group consisting of saturated alkyl radicals with carbon building blocks having from 5 to 30 carbon atoms, unsaturated alkyl radicals with carbon building blocks having from 5 to 30 carbon atoms; and
branched alkyl radicals with carbon building blocks having from 5 to 30 carbon atoms and are bound either directly or via aryl groups to a group selected from the group consisting of the hydrophilic group Y and the head group X.

* * * * *